United States Patent [19]

Engel

[11] 4,263,319

[45] Apr. 21, 1981

[54] 4-SUBSTITUTED-2-INDANOL INSECTICIDAL ESTER DERIVATIVES

[75] Inventor: John F. Engel, Medina, N.Y.

[73] Assignee: FMC Corporation, Philadelphia, Pa.

[21] Appl. No.: 42,372

[22] Filed: May 24, 1979

Related U.S. Application Data

[63] Continuation-in-part of Ser. No. 927,198, Jul. 24, 1978, abandoned, which is a continuation-in-part of Ser. No. 870,973, Jan. 20, 1978, abandoned.

[51] Int. Cl.³ .................. A01N 53/00; C07C 61/04; C07C 61/13
[52] U.S. Cl. .................................. 424/305; 424/306; 424/308; 560/8; 560/18; 560/105; 560/124; 568/808
[58] Field of Search .................. 560/8, 18, 124, 105; 424/305, 306, 308

[56] References Cited

U.S. PATENT DOCUMENTS

| | | | |
|---|---|---|---|
| 3,647,857 | 3/1972 | Morgan | 560/124 |
| 4,024,163 | 5/1977 | Elliott et al. | 260/347.4 |
| 4,157,397 | 6/1979 | Engel | 424/274 |
| 4,160,842 | 7/1979 | Engel | 424/274 |
| 4,183,948 | 1/1980 | Huff | 424/304 |

FOREIGN PATENT DOCUMENTS

| | | |
|---|---|---|
| 858137 | 2/1978 | Belgium . |
| 863151 | 7/1978 | Belgium . |
| 46-06918 | 2/1971 | Japan . |
| 46-40617 | 12/1971 | Japan . |
| 46-40618 | 12/1971 | Japan . |
| 52-14749 | 2/1977 | Japan . |

OTHER PUBLICATIONS

Nakada et al., Agric. Biol. Chem., vol. 42 (1978) p. 1357.
Elliot, Snythetic Pyrethroids, ACS Symposium Series, No. 42, American Chemical Society, Washington, D.C. (1977), Chapter 1, pp. 4, 5 & 18, Chapter 3, p. 39, Chapter 4 p. 4 and Chapter 5 pp. 55 & 56.

*Primary Examiner*—Richard Raymond
*Attorney, Agent, or Firm*—Robert M. Kennedy; H. Robinson Ertelt; Robert L. Andersen

[57] ABSTRACT

Novel compounds of the formula

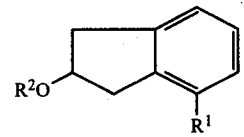

are disclosed in which $R^1$ is a phenyl, phenoxy, phenylthio, benzyl or heterocyclic radical which may be substituted, and $R^2$ is hydrogen, a substituted-vinylcyclopropanecarbonyl group, a tetramethylcyclopropanecarbonyl group, or a 1-(substituted-phenyl)-2-methylpropylcarbonyl group. The compounds wherein $R^2$ is other than hydrogen are insecticides.

10 Claims, No Drawings

4-SUBSTITUTED-2-INDANOL INSECTICIDAL ESTER DERIVATIVES

The present invention is a continuation in part of U.S. Ser. No. 927,198, filed July 24, 1978, now abandoned which is a continuation in part of Ser. No. 870,973, filed Jan. 20, 1978, now abandoned, and is directed to a novel alcohol for use in preparing cyclopropanecarboxylate and related insecticides, to insecticides employing this alcohol, and to an insecticidal method and composition. More particularly, the invention is directed to a 4-substituted-2-indanol and insecticidal esters thereof.

Pyrethrins, naturally occurring extracts of chrysanthemum flowers, have long been of interest as insecticides. Since elucidation of the structures of these compounds, synthesis efforts have been directed toward preparation of related compounds having enhanced insecticidal activity and improved stability toward air and light. Since a prerequisite for insecticidal activity of pyrethroids is the presence in one molecule of an appropriate acid moiety and an appropriate alcohol moiety, research in the art has been directed toward novel acid and/or alcohol radicals. Noteworthy advances in the area of alcohol research were the discovery of 5-benzyl-3-furylmethyl alcohol, then of the more photostable 3-phenoxybenzyl alcohol (see *Synthetic Pyrethroids*, ACS Symposium Series, No. 42, M. Elliott, Ed., American Chemical Society, Washington, D.C. 1977, Chapter 1). Similarly significant advances have been made in pyrethroid acid research. The commercial insecticide permethrin, the common name for 3-phenoxyphenylmethyl 3-(2,2-dichloroethenyl)-2,2-dimethylcyclopropanecarboxylate, exemplifies use of both newer acid and alcohol moieties in a single compound.

The present invention provides a novel indanyl alcohol and certain ester derivatives thereof which have a high level of insecticidal activity.

In this application, the term "lower" as applied to an aliphatic hydrocarbon group means having 1 to 6 carbon atoms, preferably 1 to 4 carbon atoms. The term "halo" or "halogen" means bromine, chlorine or fluorine. The term "haloalkyl" means an alkyl group of 1 to 3 carbon atoms substituted with 1 or more halogen atoms. The term "insecticide" is used in its broadest sense, and includes compounds possessing activity against true insects, acarids, and other household, veterinary or crop pests of the phylum Arthropoda. These definitions are applicable throughout the specification and claims except where a contrary meaning is clearly indicated.

The novel compounds of this invention have the general formula

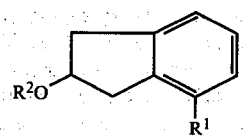

I in which $R^1$ is a phenyl, phenoxy, phenylthio, benzyl or heterocyclic radical which may be substituted with halogen, lower alkyl, halo(lower)alkyl, lower alkoxy, lower alkylthio, cyano or nitro; particularly halogen or lower alkyl. The heterocyclic radical is advantageously a 5 or 6 membered ring consisting of carbon and 1 to 3 ring members selected from oxygen, nitrogen, and sulfur. Suitable heterocyclic radicals include furanyl, thienyl, pyridyl, pyrimidyl, oxazolyl, isoxazolyl, thiazolyl, and isothiazolyl.

$R^2$ is hydrogen; 2,2,3,3-tetramethylcyclopropylcarbonyl; 1-(substituted-phenyl)-2-methylpropyl-1-carbonyl, particularly 1-(4-chlorophenyl)-2-methylpropyl-1-carbonyl; or a group of the formula:

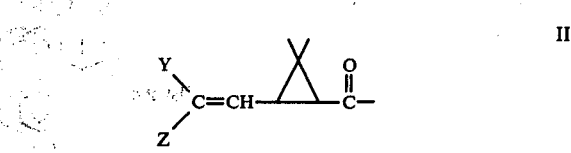

II wherein Y and Z, the same or different, are hydrogen, halogen, lower alkyl, perhalo(lower)alkyl, phenyl which may be substituted with halogen or lower alkyl, or phenylthio which may be substituted with halogen or lower alkyl, with the proviso that one of Y and Z is other than hydrogen. The novel alcohols are the compounds in which $R^2$ is hydrogen whereas in the insecticidal compounds $R^2$ is other than hydrogen.

Particularly useful insecticides of the present invention are the cyclopropanecarboxylates in which one of Y and Z is halogen, such as chlorine or bromine, and the other, the same or different, is halogen or a perhaloalkyl group such as trihalomethyl, and $R^1$ is phenyl.

The cyclopropanecarboxylates having the acid residue of formula II have cis and trans isomeric forms, i.e., the carboxy and the substituted vinyl groups at the 1 and 3 positions of the cyclopropane ring are either cis or trans with respect to each other. Preparation of these compounds will usually yield a mixture of the cis and trans isomers, designated herein as cis,trans, in which the ratio of cis to trans may vary over a wide range. For purposes of this application the designations cis and trans are assigned in accordance with P. E. Burt, et al., Pestic. Sci., 5 791–799 (1974). The compounds where Y is different from Z may also exist as E or Z isomers or as mixtures of E and Z isomers, designated E,Z, depending upon the spatial relationship of substituents on the α-carbon of the vinyl group to those on the β-carbon of the vinyl group.

In the cyclopropanecarboxylate art it is known there may be substantial differences in the level of insecticidal activity of the cis and trans isomers. In general, as between the cis and trans isomer of a given cyclopropanecarboxylate, the cis isomer is usually more active than the trans and also more active than the cis,-trans mixture. Similar differences in activity may also occur with respect to the E and Z isomers.

Unless a contrary intent is specifically expressed, this invention embodies and includes both cis and trans isomeric forms of the claimed compounds as well as mixtures thereof wherein the cis to trans ratio is within the range of 0:100 to 100:0. Similarly, the individual E and Z isomers, as well as the mixtures, are contemplated by and within the scope of the invention. The various enantiomers of the claimed compounds and mixtures of them are also included within the scope of the invention.

The novel alcohols of this invention may be prepared in a number of ways. The schemata below for 4-phenyl-2-indanol is illustrative of methods by which the alcohols can be prepared.

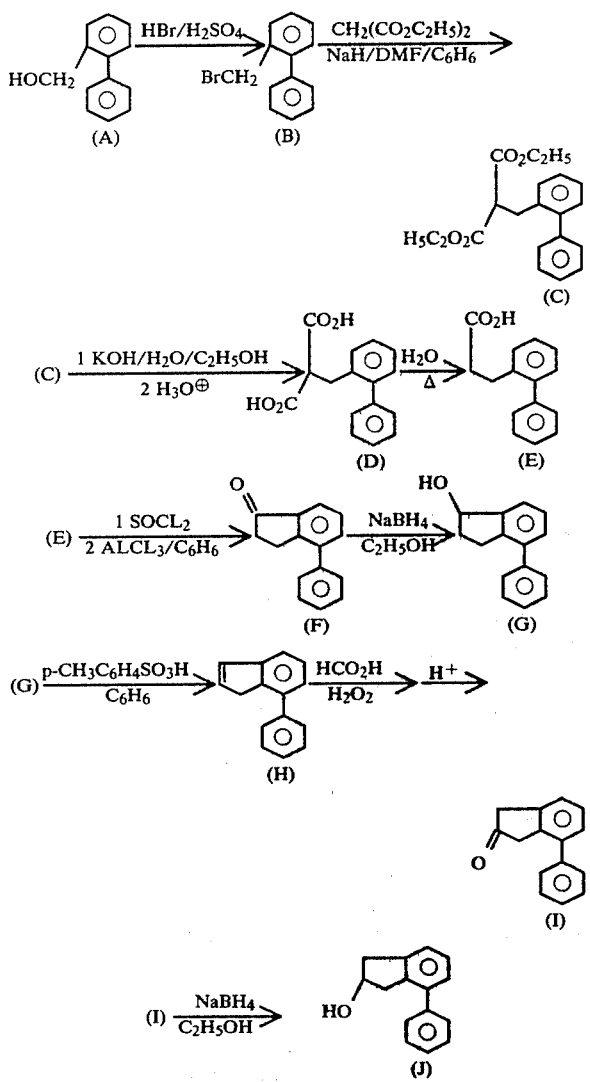

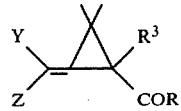

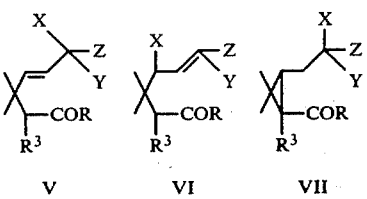

The insecticidal compounds having the acid residue of formula II may be prepared from alkanoates of the formula

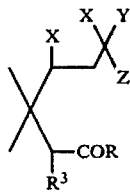
III in which Y and Z are defined as above; R is lower alkoxy, such as methoxy or ethoxy, or a 4-substituted-2-indanyloxy moiety from an alcohol of formula I; $R^3$ is hydrogen, lower alkylcarbonyl, lower alkoxycarbonyl, or cyano, preferably hydrogen; and X is chloro or bromo. Example 2 illustrates a method for preparation of the alkanoate intermediates of Formula III whereby a lower alkyl 3,3-dimethyl-4-pentenoate is allowed to react with a compound of the formula $X_2C(Y)(Z)$ wherein X, Y, and Z are as defined above.

Dehydrohalogenation of the compound of formula III followed, if necessary, by hydrolysis of the ester and, also if necessary, halogenation of the resulting carboxyl group gives a compound of the formula

IV in which R is lower alkoxy, hydroxy, halogen, or a 4-substituted-2-indanyloxy moiety from an alcohol of formula I, and Y, Z and $R^3$ are as defined above. The dehydrohalogenation reaction may proceed through one or more intermediates of the formulas:

V    VI    VII and may be conducted in a single step by elimination of 2 equivalents of hydrogen halide, HX, to give a compound of formula VI directly, or in multiple steps under conditions allowing a sequential elimination of the 2 equivalents of HX in separate reactions. These intermediates or mixtures thereof may be recovered if desired. The compound of formula IV is then converted to the compound of formula I by methods known to the art, for example, by removing $R^3$ (if other than hydrogen) and, where R is lower alkoxy, hydroxy, or halogen, esterifying or transesterifying with a 4-substituted-2-indanol of formula I ($R^2$ is hydrogen).

The examples which follow illustrate preparation of the insecticidal compounds and novel alcohol intermediates therefor in accordance with the general method described above. In the examples all temperatures are in degrees centigrade, all pressures are in mm. Hg, and reduced pressure for concentrations of liquid was produced by a water aspirator unless otherwise specified.

Example 1 illustrates the preparation of compounds of formula I wherein $R^2$ is hydrogen.

EXAMPLE 1

SYNTHESIS OF 4-PHENYL-2-INDANOL

A. Preparation of 2-(bromomethyl)biphenyl

A stirred solution of 58.9 g (0.319 mole) of 2-biphenylmethanol and 6 ml of concentrated sulfuric acid in 67 ml of aqueous 48% hydrobromic acid was heated under reflux for 5 hours. The reaction mixture was cooled to ambient temperature, poured into ice-water, and the resulting mixture extracted with three portions of 100 ml each of diethyl ether. The combined extracts were washed with 50 ml of a saturated aqueous solution of sodium bicarbonate, then with 50 ml of water. The organic layer was dried with magnesium sulfate, filtered and the filtrate concentrated under reduced pressure to give 76.8 g of 2-(bromomethyl)biphenyl as a residual oil. The nmr and ir spectra were consistent with the proposed structure.

B. Preparation of diethyl (2-phenylbenzyl)malonate

A stirred mixture of 12.5 g (0.54 mole) of sodium hydride (25 g of a 50% dispersion in mineral oil) in 300 ml of dimethylformamide and 900 ml of benzene was placed under a nitrogen atmosphere and cooled to 0° C. To this mixture, 104.3 g (0.9 mole) of diethyl malonate was added dropwise during a 5 minute period and the mixture was stirred until hydrogen evolution ceased. 2-(Bromomethyl)-biphenyl (117 g, 0.47 mole) was then added at 0° C. Upon complete addition the reaction mixture was stirred at 0° C. for 30 minutes, then was allowed to warm to ambient temperature with stirring for one hour. The reaction mixture was poured into 500 ml of water, the layers separated, and the aqueous layer washed with two portions of 250 ml each of diethyl ether. The organic layer was combined with the ether washings, and the whole was washed with one portion of 500 ml of aqueous 5% hydrochloric acid, one portion of 500 ml of water, one portion of 300 ml of a solution saturated with sodium bicarbonate, and finally, one portion of 500 ml of water. The organic layer was dried with magnesium sulfate, filtered, and the filtrate concentrated under reduced pressure to an oil residue. The oil was distilled under reduced pressure to give 149.0 g of diethyl (2-phenylbenzyl)malonate; b.p. 175°–180° C./0.8–0.9 mm. The nmr spectrum was consistent with the proposed structure.

C. Preparation of (2-phenylbenzyl)malonic acid

A stirred solution of 149.0 g (0.456 mole) of diethyl (2-phenylbenzyl)malonate and 56.1 g (1.0 mole) of potassium hydroxide in 50 ml of water and 500 ml of ethanol was heated under reflux for 3 hours. The reaction mixture was allowed to cool to ambient temperature and stand for 60 hours. The ethanol was removed by distillation and the residue slurried in 400 ml of water. The mixture was extracted with one portion of 250 ml of diethyl ether. The aqueous phase was separated and acidified with concentrated hydrochloric acid, then extracted with two portions of 250 ml each of diethyl ether. The two extracts of the acidified aqueous phase were combined, dried with magnesium sulfate, filtered, and the filtrate concentrated under reduced pressure to give (2-phenylbenzyl)malonic acid as a pale yellow oil. The oil was used directly in the next step of this reaction sequence.

D. Preparation of 3-(2-biphenyl)propionic acid

A solution of 124.2 g (0.46 mole) of the oil from step C of this Example in 500 ml of water was heated under reflux for 16 hours. The reaction mixture was cooled, and the product was collected by filtration to give, after recrystallization from ethanol-water, 92.9 g of 3-(2-biphenyl)propionic acid. The nmr spectrum was consistent with the proposed structure.

Analysis calc'd for $C_{15}H_{14}O_2$: C 79.62, H 6.24, Found: C 79.84, H 5.98.

E. Preparation of 4-phenyl-1-indanone

A solution of 92.9 g (0.41 mole) of 3-(2-biphenyl)propionic acid in 100 ml of thionyl chloride was stirred at ambient temperature for 16 hours. The excess thionyl chloride was removed by distillation followed by co-distillation with three 50 ml portions of benzene.

The residue was dissolved in 150 ml of benzene and was added dropwise at 10° C. over 15 minutes to a stirred mixture of 71.0 g (0.53 mole) of aluminum chloride in 900 ml of benzene. Upon complete addition the reaction mixture was stirred at 10° C. for 110 minutes then poured into 1000 ml of ice-water and stirred until the ice melted. The aqueous phase was separated and extracted with two portions of 100 ml each of diethyl ether. The ether extracts and the organic phase were combined and washed with a 10% aqueous solution of sodium hydroxide, then with two portions of water. The combined extracts were dried with magnesium sulfate, filtered, and the filtrate concentrated under reduced pressure to give, as a brown crystalline solid, 85.4 g of 4-phenyl-1-indanone, m.p. 85°–90° C. The product was used without further purification.

A sample was recrystallized for analytical purposes. The nmr spectrum was consistent with the proposed structure.

Analysis calc'd for $C_{15}H_{20}O$: C 86.50, H 5.81; Found: C 86.63, H 5.74.

F. Preparation of 4-phenyl-1-indanol

To a stirred solution of 20.8 g (0.10 mole) of 4-phenyl-1-indanone in 150 ml of ethanol was added portionwise 2.0 g (0.06 mole) of sodium borohydride. During the addition the reaction temperature rose to 33° C. Upon complete addition the reaction mixture was allowed to cool to ambient temperature and was stirred for 16 hours. The reaction mixture was mixed in water and concentrated under reduced pressure. A precipitate, which developed during concentration of the aqueous solution, was collected, dried, then recrystallized from toluene-hexane to give 17.3 g of 4-phenyl-1-indanol; m.p. 80.5°–81.5° C. The nmr spectrum was consistent with the proposed structure.

Analysis calc'd for $C_{15}H_{14}O$: C 85.68, H 6.71; Found: C 85.63, H 6.70.

G. Preparation of 7-phenyl-1H-indene

A stirred solution of 16.7 g (0.08 mole) of 4-phenyl-1-indanol and 0.1 g of p-toluenesulfonic acid in 180 ml of benzene was heated under reflux for one hour as by-product water was collected in a Dean-Stark trap. The reaction mixture was washed with two portions of 50 ml of a 5% aqueous solution of sodium bicarbonate, then with one portion of 50 ml of water. The organic phase was dried with magnesium sulfate, filtered, and the filtrate concentrated under reduced pressure, keeping the temperature under 50° C., to give 14.8 g of 7-phenyl-1H-indene. The nmr specturm was consistent with the proposed structure.

Analysis calc'd for $C_{15}H_{12}$: C 93.71, H 6.29; Found: C 93.47, H 6.31.

H. Preparation of 4-phenyl-2-indanone

A stirred solution of 53.2 ml of formic acid and 10.5 ml of 30% hydrogen peroxide was heated to 35° C., and 14.5 g (0.075 mole) of 7-phenyl-1H-indene was added dropwise causing the reaction mixture temperature to rise to 41° C. Upon complete addition the reaction mixture was allowed to cool to ambient temperature and was stirred for 16 hours. The reaction mixture was concentrated under reduced pressure to give a residual semi-solid which was subjected to steam distillation in the presence of aqueous dilute sulfuric acid. The steam distillates were filtered to give 1.84 of 4-phenyl-2-indanone; m.p. 133°–136° C. The nmr and the ir spectra were consistent with the proposed structure.

I. Preparation of 4-phenyl-2-indanol

To a stirred mixture of 0.30 g (0.0014 mole) of 4-phenyl-2-indanone in 10 ml of ethanol was added portionwise 0.03 g (0.0008 mole) of sodium borohydride. The resulting yellow colored solution was stirred at ambient temperature for 1.5 hours, then concentrated, and 50 ml of water was added. The mixture was extracted with two portions of 50 ml each of diethyl ether. The extracts were combined, dried with sodium sulfate, filtered and the filtrate concentrated under reduced pressure to give, after recrystallization from hexane, 0.13 g of 4-phenyl-2-indanol. The nmr and ir spectra were consistent with the proposed structure.

Example 2 illustrates the preparation of compounds of formula III.

EXAMPLE 2

SYNTHESIS OF ETHYL 3,3-DIMETHYL-4,6,6-TRICHLORO-7,7,7-TRIFLUOROHEPTANOATE

A stirred solution of 44.6 (0.267 mole) of ethyl 3,3-dimethyl-4-pentenoate, 100 g (0.533 mole) of 1,1,1-trichlorotrifluoroethane, 0.27 g (0.0027 mole) of cuprous chloride, and 8.2 g (0.134 mole) of ethanolamine in 270 ml of tertiary butyl alcohol, under a nitrogen atmosphere, was heated at reflux for 16 hours. The reaction mixture was cooled to ambient temperature and extracted with three portions of 100 ml each of diethyl ether. A precipitate formed in the extracts, and was removed by vacuum filtration. The filter cake was washed with two portions of 25 ml each of diethyl ether. The ether extracts were combined with the washings, and the whole was concentrated under reduced pressure to an oily residue. Remaining volatile components were removed from the residue under further reduced pressure using a vacuum pump. The residue was subjected to distillation under reduced pressure to give 78.3 g of ethyl 3,3-dimethyl-4,6,6-trichloro-7,7,7-trifluoroheptanoate; bp 85°–87° at 0.12–0.15 mm. The nmr spectrum was consistent with the assigned structure.

Examples 3 and 4 illustrate preparation of the lower alkyl esters of formula IV. Example 3 is a two-step process via the intermediate of formula VII. Example 4 is a one-step process.

EXAMPLE 3

SYNTHESIS OF METHYL CIS,TRANS-3-(2-CHLORO-3,3,3-TRIFLUORO-1-PROPENYL)-2,2-DIMETHYLCYCLOPROPANECARBOXYLATE

A. Preparation of methyl cis,trans-3-(2,2-dichloro-3,3,3-trifluoropropyl)-2,2-dimethylcyclopropanecarboxylate A stirred solution of 37.0 g (0.112 mole) of methyl 3,3-dimethyl-4,6,6-trichloro-7,7,7-trifluoroheptanoate, 50 ml of tert-butyl alcohol, 50 ml of dimethylformamide, and 50 ml of hexane, under an argon atmosphere, was cooled to −5° C. To the stirred solution was added dropwise a solution of 16.4 g (0.14 mole) of potassium tert-butoxide in 200 ml of tert-butyl alcohol at such a rate so as to maintain the reaction mixture temperature at −3° to −5° C. Upon complete addition, the reaction mixture was stirred for 4 hours at −3° to −5° C., then poured into a solution of 8.0 g of ammonium chloride in 250 ml of water. The mixture was extracted with two portions of 200 ml each of diethyl ether. The combined ether extracts were washed with two portions of 200 ml each of water. The ether layer was dried with sodium sulfate and filtered. The filtrate was evaporated under reduced pressure to a residual oil. The oil was distilled under reduced pressure to give 19.8 g of methyl cis,-trans-3-(2,2-dichloro-3,3,3-trifluoropropyl)-2,2-dimethylcyclopropanecarboxylate; b.p. 55°–57° C./0.09 mm Hg. The ir and the nmr spectra were consistent with the proposed structure.

Analysis calc'd for $C_{10}H_{13}Cl_2F_3O_2$: C 40.98; H 4.47; Found: C 41.50; H 4.41.

B. Synthesis of methyl cis,trans-3-(2-chloro-3,3,3-trifluoro-1-propenyl)-2,2-dimethylcyclopropanecarboxylate.

A stirred solution of 30.6 g (0.105 mole) of methyl cis,trans-3-(2,2-dichloro-3,3,3-trifluoropropyl)-2,2-dimethylcyclopropanecarboxylate and 17.6 g (0.116 mole) of 1,5-diazabicyclo[5.4.0]undec-5-ene in 100 ml of dimethylformamide was heated at 100° C. for 4 hours. The reaction mixture was cooled and poured into a solution of 37.2 ml of concentrated hydrochloric acid in 300 ml of water. The mixture was extracted with three portions of 200 ml each of diethyl ether. The combined ether extracts were washed with an aqueous saturated solution of sodium chloride. The ether layer was dried with sodium sulfate and filtered. The filtrate was evaporated under reduced pressure to give a residual oil. The oil was dissolved in hexane, treated with decolorizing carbon, and filtered. The filtrate was evaporated under reduced pressure to a residual oil. The oil was distilled under reduced pressure to give in three fractions 10.0 g of methyl cis,trans 3-(2-chloro-3,3,3-trifluoro-1-propenyl)-2,2-dimethylcyclopropanecarboxylate; b.p. 40°–60° C./0.05 mm. The ir and the nmr spectra were consistent with the proposed structure. The nmr spectra indicated an 88:12 mixture of cis:trans isomers.

Analysis calc'd for $C_{10}H_{12}ClF_3O_2$: C 46.80; H 4.71; Found: C 46.91; H 4.79.

EXAMPLE 4

SYNTHESIS OF ETHYL CIS,TRANS-3-(2-CHLORO-3,3,3-TRIFLUORO-1-PROPENYL)-2,2-DIMETHYLCYCLOPROPANECARBOXYLATE

To a stirred solution of 78.3 g (0.228 mole) of ethyl 3,3-dimethyl-4,6,6-trichloro-7,7,7-trifluoroheptanoate in 200 ml of distilled ethanol was added dropwise at ambient temperature 500 ml of an ethanolic solution of sodium ethoxide prepared from 11.5 g of metallic sodium (0.50 mole). After complete addition, the reaction mixture was stirred for one hour at ambient temperature, then allowed to stand for 18 hours. The cloudy reaction mixture was filtered and the filtrate evaporated under reduced pressure to give a residue. The residue was slurried in 200 ml of water, and the mixture was extracted with three portions of 50 ml each of diethyl ether. The combined extracts were dried with sodium sulfate and filtered. The filtrate was evaporated under reduced pressure to give, as a residual oil, 58.5 g of ethyl cis,trans-3-(2-chloro-3,3,3-trifluoro-1-propenyl)-2,2-dimethylcyclopropanecarboxylate. The nmr and the ir spectra were consistent with the assigned structure and indicated the product was a mixture of approximately equal parts of cis and trans isomers.

Examples 5 and 6 illustrate preparation of the individual cis and trans isomers of the free acids of formula IV.

EXAMPLE 5

SYNTHESIS OF TRANS AND CIS,TRANS-3-(2-CHLORO-3,3,3-TRIFLUORO-1-PROPENYL)-2,2-DIMETHYLCYCLOPROPANECARBOXYLIC ACID

A solution of 16.2 g (0.06 mole) of ethyl cis, trans-3-(2-chloro-3,3,3-trifluoro-1-propenyl)-2,2-dimethylcyclopropanecarboxylate in 94 ml (0.078 mole) of a stock solution containing 3.34 g of sodium hydroxide, 94 ml of ethanol and 6 ml of water was stirred while heating under reflux for a period of 18 hours. The reaction mixture was concentrated under reduced pressure, 25 ml of water was added, and the mixture was acidified to pH1 using 6 N hydrochloric acid. The acidified mixture was extracted with two portions of 50 ml each of diethyl ether. The combined extracts were dried with magnesium sulfate and filtered. The filtrate was evaporated under reduced pressure to give a residue. The residue was heated with 50 ml of hexane. The hot hexane was decanted from a tarry residue and cooled to yield a solid precipitate, which was collected by filtration, then dried to give 3.3 g of solid, m.p. 97°–103° C. Concentration of the mother liquor provided a second fraction of solid weighing 0.8 g, m.p. 96°–103° C. Nmr spectra of the two fractions indicated the solids were each trans-3-(2-chloro-3,3,3-trifluoro-1-propenyl)-2,2-dimethylcyclopropanecarboxylic acid. The mother liquor was evaporated to a residue. The residue was taken up in 50 ml of hexane and the solution cooled in a freezer for 18 hours. A solid precipitate was collected by filtration and dried to give 4.3 g of a solid, m.p. 64°–74° C. An nmr spectrum indicated the solid was a 50/50 mixture of cis and trans isomers of 3-(2-chloro-3,3,3-trifluoro-1-propenyl)-2,2-dimethylcyclopropanecarboxylic acid.

EXAMPLE 6

SYNTHESIS OF CIS AND CIS,TRANS-3-(2-CHLORO-3,3,3-TRIFLUORO-1-PROPENYL)-2,2-DIMETHYLCYCLOPROPANECARBOXYLIC ACID

A stirred solution of 90.0 g (0.35 mole) of methyl cis,trans-3-(2-chloro-3,3,3-trifluoro-1-propenyl)-2,2-dimethylcyclopropanecarboxylate (approximately 90% cis, prepared in accordance with Example 3B), 5.4 ml of concentrated sulfuric acid and 13.8 ml of water in 138 ml of acetic acid was heated under reflux for 1 hour. The reaction mixture was cooled and extracted with two portions of 100 ml each of diethyl ether. The combined extracts were dried with sodium sulfate, filtered, and the filtrate concentrated under reduced pressure to a solid residue. The residue was digested with 300 ml of hexane and the hexane solution was decanted from a dark, tarry residue and allowed to cool to ambient temperature. A solid precipitate formed and was collected by filtration to give 42.4 g of cis-3-(2-chloro-3,3,3-trifluoro-1-propenyl)-2,2-dimethylcyclopropanecarboxylic acid, as determined by NMR spectroscopy. A melting point was not determined. The melting point of another sample of cis acid prepared at a different time was 108°–110° C. The filtrate was concentrated and cooled to give 5.1 g of solid, identified by NMR spectroscopy to be a 50:50 mixture of cis,trans-3-(2-chloro-3,3,3-trifluoro-1-propenyl)-2,2-dimethylcyclopropanecarboxylic acid. The filtrate was cooled in dry ice to give an additional 8.1 g of a 50:50 mixture of the cis,trans isomers.

Examples 7 and 8 illustrate preparation of the acid halides of formula IV.

EXAMPLE 7

SYNTHESIS OF TRANS-3-(2-CHLORO-3,3,3-TRIFLUORO-1-PROPENYL)-2,2-DIMETHYLCYCLOPROPANECARBONYL CHLORIDE

To a stirred solution of 4.1 g (0.0173 mole) of trans-3-(2-chloro-3,3,3-trifluoro-1-propenyl)-2,2-dimethylcyclopropanecarboxylic acid in 40 ml of toluene at ambient temperature was added 1.7 g (0.022 mole) of pyridine, then 2.6 g (0.022 mole) of thionyl chloride in 25 ml of toluene. Upon complete addition the reaction mixture was stirred at ambient temperature for 17 hours. The reaction mixture was filtered through diatomaceous earth, and the filtrate was evaporated under reduced pressure to give 3.8 g of trans-3-(2-chloro-3,3,3-trifluoro-1-propenyl)-2,2-dimethylcyclopropanecarbonyl chloride. The ir spectrum was consistent with the assigned structure.

EXAMPLE 8

SYNTHESIS OF CIS-3-(2-CHLORO-3,3,3-TRIFLUORO-1-PROPENYL)-2,2-DIMETHYLCYCLOPROPANECARBONYL CHLORIDE

A stirred solution of 10.0 g (0.04 mole) of cis-3-(2-chloro-3,3,3-trifluoro-1-propenyl)-2,2-dimethylcyclopropanecarboxylic acid in 100 ml of toluene was heated to 80° C. To this solution at 80° C. was added dropwise over 10 minutes a solution of 10.5 g (0.08 mole) of oxalyl chloride in 5 ml of toluene, and the whole heated at 80° C. for 26 hours. The toluene and excess oxalyl chloride were removed by distillation to give a residual oil which was distilled under reduced pressure using a Kugelrohr distilling system to give 8.2 g of cis-3-(2-chloro-3,3,3-trifluoro-1-propenyl)-2,2-dimethylcyclopropanecarbonyl chloride; b.p. 85° C./0.09 mm. The nmr and ir spectra were consistent with the proposed structure.

Examples 9 and 10 illustrate preparation of compounds of formula I wherein $R^2$ is other than hydrogen.

EXAMPLE 9

SYNTHESIS OF 4-PHENYL-2-INDANYL CIS-3-(2-CHLORO-3,3,3-TRIFLUORO-1-PROPENYL)-2,2-DIMETHYLCYCLOPROPANECARBOXYLATE

A stirred solution of 0.25 g (0.0012 mole) of 4-phenyl-2-indanol and 0.11 g (0.0014 mole) of pyridine in 10 ml of toluene was cooled to 5° C., and a solution of 0.28 g (0.0011 mole) of cis-3-(2-chloro-3,3,3-trifluoro-1-propenyl)-2,2-dimethylcyclopropanecarbonyl chloride, prepared in accordance with Example 8, in 5 ml of toluene was added portionwise. Upon complete addition the reaction mixture was stirred at ambient temperature for 2 hours. The reaction mixture was filtered and the filtrate concentrated under reduced pressure to a residual oil. The oil was placed on a silica gel pad, and the product was eluted with 50 ml of 1:1 hexane:toluene. The eluate was concentrated under reduced pressure at 100°–115° C./0.02 mm using a Kugelrohr distilling system to give 0.12 g of 4-phenyl-2-indanyl cis-3-(2- chloro-3,3,3-trifluoro-1-propenyl)-2,2-dimethylcyclopropanecarboxylate. The nmr spectrum was consistent with the proposed structure.

Analysis calc'd for $C_{24}H_{22}ClF_3O_2$: C 66.28; H 5.10; Found: C 65.76; H 5.28.

EXAMPLE 10

SYNTHESIS OF 4-PHENYL-2-INDANYL CIS,TRANS-3-(2,2-DICHLOROETHENYL)-2,2-DIMETHYLCYCLOPROPANECARBOXYLATE

A solution of 0.64 g (0.003 mole) of 4-phenyl-2-indanol, 0.70 g (0.003 mole) of cis,trans 3-(2,2-dichloroethenyl)-2,2-dimethylcyclopropanecarbonyl chloride, and 0.24 g (0.003 mole) of pyridine, in 20 ml of benzene was stirred at ambient temperature for 16 hours, then mixed with 50 ml of water. The organic layer was separated and the aqueous layer was washed with 50 ml of diethyl ether. The combined organic layers were washed with 100 ml of aqueous dilute hydrochloric acid, then with 100 ml of a 10% aqueous solution of sodium hydroxide, and finally, with water. The organic layer was dried with magnesium sulfate, filtered, and the filtrate concentrated under reduced pressure to a residual oil. The oil was subjected to column chromatography, eluting with benzene. The appropriate fractions were combined to give 1.1 g of 4-phenyl-2-indanyl cis,trans-3-(2,2-dichloroethenyl)-2,2-dimethylcyclopropanecarboxylate.

Analysis calc'd for $C_{23}H_{22}Cl_2O_2$: C 68.83; H 5.53; Found: C 68.59; H 5.79.

In the method aspect of this invention, an effective insecticidal amount of the compound of formula I wherein $R^2$ is other than hydrogen is applied to the locus where insect control is desired, i.e., to the insect itself or to the foliage or seeds of agricultural plants. The compounds are useful for the control of household, veterinary, and crop insects and may be applied as technical material or as formulated product. Typical formulations include compositions of the active ingredient in combination with an agriculturally acceptable carrier or extender, preferably with a surface active agent, and optionally with other active ingredients. Suitable formulations include granules, powders, or liquids, the choice varying with the type of pest and environmental factors present at the particular locus of infestation. Thus, the compounds may be formulated as granules of various sizes, as dusts, as wettable powders, as emulsifiable concentrates, as solutions, as dispersions, as controlled release compositions, and the like. A typical formulation may vary widely in concentration of active ingredient depending upon the particular agent used, the additives and carriers used, other active ingredients, and the desired mode of application. With due consideration to these factors the active ingredient of a typical formulation may, for example, be suitably present at a concentration of about 0.01% up to about 99.5%, preferably 0.1% up to 90%, of the formulation. An agriculturally acceptable carrier may comprise about 99.5% by weight to as low as about 0.5% by weight of the formulation. Compatible surface active agents, if employed in a formulation, may be present at various concentrations, suitably in the range of 1 to 30% by weight of the formulation.

The formulation may be used as such or diluted to a desired use dilution with a diluent or carrier suitable for facilitating dispersion of the active ingredients. A concentration of the active ingredient in the use dilution may be in the range of 0.01% to about 10% by weight.

Many variations of spraying, dusting, and controlled or slow release compositions of a type known in the art may be used by substituting or adding an insecticidal compound or compounds of this invention into the compositions known or apparent to the art.

The insecticidal compounds of this invention may be formulated and applied with other compatible active agents including nematacides, insecticides, acaracides, fungicides, plant regulators, herbicides, fertilizers, and the like.

In applying these compounds, whether alone or with other agricultural chemicals, an effective insecticidal amount of the active ingredient must be applied. While the application rate will vary widely depending on the choice of compound, formulation, mode of application, plant species being protected, planting density and other like factors, a suitable use rate for agricultural crops may be in the range of 0.005 to 3 k/ha, preferably 0.01 to about 1 k/ha.

The insecticidal compounds of this invention were tested for insecticidal activity as described in Examples 11 and 12 below.

EXAMPLE 11

Initial Contact Activity:

The test compound was dissolved in 5–10 ml of acetone containing 0.25% acetylphenoxypolyethylethanol. This solution was dispersed in a solution of 90% water, 9.75% acetone, and 0.25% acetylphenoxypolyethylethanol to give a solution having 512 ppm (w/w) active ingredient. Aliquots of this solution were diluted with an appropriate amount of water to provide solutions containing various concentrations of active ingredient. Test organisms and techniques were as follows: The activity against Mexican bean beetle (*Epilachna varivestis* Muls.) and southern armyworm (*Spodoptera eridania* [Cram.]) was evaluated by spraying the leaves of pinto bean plants with the test solution and infesting with 3rd instar larvae after the foilage had dried. The activity against the pea aphid (*Acyrthosiphon pisum* [Harris]) was evaluated on broad bean plants whose leaves were sprayed before infestation with adult aphids. To prevent escape of the insects from the test site, the complete test plant or the incised leaves were placed in capped paper cups. The tests were transferred to a holding room at 80° C. and 50% relative humidity for an exposure period of at least 48 hours. At the end of this time the dead and living insects were counted and the percent kill was calculated. Results of these tests are summarized in the table below. Also shown in the table below for comparison are insecticidal efficacy data from these tests for the commercial insecticide permethrin, 3-phenoxybenzyl (+) cis,trans-3-(2,2-dichloroethenyl)-2,2-dimethylcyclopropanecarboxylate. Mortality figures in parentheses are from retests.

The compound of Example 10 was more active than permethrin against Mexican bean beetle and pea aphid, but less active than permethrin against Southern armyworm. The compound of Example 9 was superior in activity to permethrin against all three insect species. Relative to permethrin, the compounds of Examples 9 and 10 showed outstanding activity against pea aphid.

| | INITIAL CONTACT ACTIVITY | | | |
|---|---|---|---|---|
| Compound | Percent Kill at Indicated Concentration (ppm) Mexican Bean Beetle | | | |
| of Example | 16 | 8 | 6.5 | 3.2 |
| 9 | — | — | 100 | 100 |
| 10 | 100(100) | 85(80) | — | — |
| Permethrin | 50(55) | 35(25) | — | — |
| | Southern Armyworm | | | |
| 9 | — | — | 100 | 80 |
| 10 | 100 | 85 | 35 | 10 |
| Permethrin | — | — | 100 | 60(7) |
| | Pea Aphid | | | |
| 9 | — | — | 100 | 100 |
| 10 | 80(100) | 80(70) | — | — |
| Permethrin | 10(30) | — | — | — |

EXAMPLE 12

Topical Application Test

The compounds of this invention were tested for insecticidal activity by applying to the insect appropriate amounts of a toxicant solution containing 5 mg/l of toxicant in acetone. The tests were read twenty-four hours after application of the toxicant solution and the percent kill determined. The commercial insecticide permethrin, 3-phenoxybenzyl (+) cis-trans-3-(2,2-dichlorovinyl)-2,2-dimethylcyclopropanecarboxylate, was used as the standard for comparison. Relative potency, based on a value of 1.0 for permethrin was determined by comparing the $LD_{50}$ for the test compound with that for the standard. The insects employed include southern armyworm (*Spodoptera eridania* [Cram.]), cabbage looper (Trichoplusia ni [Hubner]), Mexican bean bettle (*Epilachna varivestis Muls.*), beet armyworm (*Spodoptera exigua* [Hubner]), milkweed bug (*Oncopeltus faciatus* [Dallas]), tobacco budworm (*Heliothis virescens* [Fabricius]), and corn earworm (*Heliothis zea* [Boddie]). The results of these tests are shown in the table below. The insect species above are designated in the table respectively, as SAW, CL, MBB, BAW, MWB, TBW, and CEW.

In these tests, the compound of Example 9 was generally superior to permethrin while the compound of Example 10 was generally inferior to permethrin. The compound of Example 9, which was not tested against beet armyworm, tobacco budworm or corn earworm, was less active than permethrin against Southern armyworm, and more active than permethrin against cabbage looper, Mexican bean beetle, and milkweed bug. The compound of Example 10 was less active than permethrin against Southern armyworm, cabbage looper, and corn earworm, more active than permethrin against milkweed bug, and about as active as permethrin against Mexican bean beetle, beet armyworm, and tobacco budworm.

| | TOPICAL APPLICATION TEST | | | | | | |
|---|---|---|---|---|---|---|---|
| Compound | Relative Potency Against | | | | | | |
| of Ex. | SAW | CL | MBB | BAW | MWB | TBW | CEW |
| Permethrin | $1.0^1$ | $1.0^2$ | $1.0^3$ | — | $1.0^4$ | — | — |
| 9 | 0.55 | 1.50 | 3.31 | — | 1.58 | — | — |
| Permethrin | $1.0^5$ | $1.0^6$ | $1.0^7$ | $1.0^8$ | $1.0^9$ | $1.0^{10}$ | $1.0^{11}$ |

-continued

| | TOPICAL APPLICATION TEST | | | | | | |
|---|---|---|---|---|---|---|---|
| Compound | Relative Potency Against | | | | | | |
| of Ex. | SAW | CL | MBB | BAW | MWB | TBW | CEW |
| 10 | 0.47 | 0.65 | 1.04 | 0.96 | 1.68 | 0.93 | 0.72 |

[1]$LD_{50}$ = 18 nanograms/insect [2]$LD_{50}$ = 130 nanograms/insect [3]$LD_{50}$ = 17 nanograms/insect [4]$LD_{50}$ = 700 nanograms/insect [5]$LD_{50}$ = 24 nanograms/insect [6]$LD_{50}$ = 140 nanograms/insect [7]$LD_{50}$ = 21 nanograms/insect [8]$LD_{50}$ = 1300 nanograms/insect [9]$LD_{50}$ = 640 nanograms/insect [10]$LD_{50}$ = 750 nanograms/insect [11]$LD_{50}$ = 270 nanograms/insect

I claim:

1. A compound of the formula

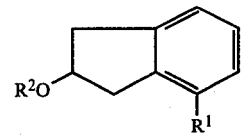

in which $R^1$ is phenyl which may be substituted with or lower alkyl, and $R^2$ is 2,2,3,3-tetramethylcyclopropylcarbonyl, 1-(4-chlorophenyl)-2-methylpropylcarbonyl, or a group of the formula

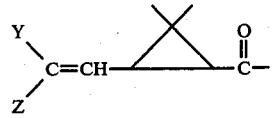

wherein Y and Z, the same or different, are hydrogen, halogen, lower alkyl, perhalo(lower)alkyl, phenyl which may be substituted with halogen or lower alkyl, or phenylthio which may be substituted with halogen or lower alkyl, with the proviso that one of Y and Z is other than hydrogen or methyl.

2. The compound of claim 1 wherein $R^2$ is a group of the formula

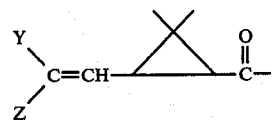

3. The compound of claim 2 wherein one of Y and Z is halogen and the other is halogen or perhaloalkyl, and $R^1$ is phenyl.

4. The compound of claim 3 wherein Y and Z are each halogen.

5. The compound of claim 4 wherein Y and Z are each chlorine.

6. The compound of claim 3 wherein one of Y and Z is halogen and the other is trifluoromethyl.

7. The compound of claim 6 wherein one of Y and Z is chlorine and the other is trifluoromethyl.

8. An insecticidal composition comprising an insecticidally effective amount of the compound of claim 1, 2, 3, 4, 5, 6 or 7 in admixture with a compatible extender or carrier.

9. A method for controlling insects which comprises applying to the insect or to a locus where control is desired an insecticidally effective amount of the compound of claim 1, 2, 3, 4, 5, 6 or 7.

10. A method for controlling insects which comprises applying to the insect or to a locus where control is desired an insecticidally effective amount of the composition of claim 8.

* * * * *

UNITED STATES PATENT AND TRADEMARK OFFICE
CERTIFICATE OF CORRECTION

PATENT NO. : 4,263,319
DATED : April 21, 1981
INVENTOR(S) : John Francis Engel

It is certified that error appears in the above—identified patent and that said Letters Patent is hereby corrected as shown below:

Column 12, line 58, "(+) cis,trans" should read --(±) cis,trans--. Column 13, line 28, "(+) cis,trans" should read --(±) cis,trans--. Column 14, line 21, "in which $R^1$ is phenyl which may be substituted with or" should read --in which $R^1$ is phenyl which may be substituted with halogen or--.

Signed and Sealed this

Eighth Day of September 1981

[SEAL]

Attest:

GERALD J. MOSSINGHOFF

Attesting Officer    Commissioner of Patents and Trademarks